US009139624B2

(12) United States Patent  
Singh et al.

(10) Patent No.: US 9,139,624 B2  
(45) Date of Patent: *Sep. 22, 2015

(54) **BIOLOGICALLY ACTIVE HEMAGGLUTININ FROM TYPE A *CLOSTRIDIUM BOTULINUM* AND METHODS OF USE**

(75) Inventors: Bal Ram Singh, Dartmouth, MA (US); Shashi Kant Sharma, New Bedford, MA (US)

(73) Assignee: Bal Ram Singh, North Dartmouth, MA (US)

( * ) Notice: Subject to any disclaimer, the term of this patent is extended or adjusted under 35 U.S.C. 154(b) by 123 days.

This patent is subject to a terminal disclaimer.

(21) Appl. No.: 12/463,925

(22) Filed: May 11, 2009

(65) Prior Publication Data

US 2010/0062024 A1    Mar. 11, 2010

Related U.S. Application Data

(63) Continuation of application No. 11/286,515, filed on Nov. 22, 2005, now Pat. No. 7,531,183, which is a continuation of application No. 09/546,727, filed on Apr. 11, 2000, now Pat. No. 6,994,859, which is a continuation of application No. 09/013,411, filed on Jan. 26, 1998, now abandoned.

(51) Int. Cl.
| | |
|---|---|
| *A61K 39/08* | (2006.01) |
| *C07K 14/33* | (2006.01) |
| *A61K 38/00* | (2006.01) |
| *A61K 39/00* | (2006.01) |

(52) U.S. Cl.
CPC ............... *C07K 14/33* (2013.01); *A61K 39/08* (2013.01); *A61K 38/00* (2013.01); *A61K 39/00* (2013.01); *A61K 2039/55555* (2013.01); *Y10S 530/825* (2013.01)

(58) Field of Classification Search
None
See application file for complete search history.

(56) References Cited

U.S. PATENT DOCUMENTS

| 5,183,462 | A | 2/1993 | Borodic | |
|---|---|---|---|---|
| 5,512,547 | A | 4/1996 | Johnson et al. | |
| 6,203,794 | B1 | 3/2001 | Dolly et al. | |
| 6,395,277 | B1 | 5/2002 | Graham | |
| 6,994,859 | B1 * | 2/2006 | Singh et al. | 424/247.1 |
| 7,501,130 | B2 | 3/2009 | Aoki et al. | |
| 2001/0021695 | A1 | 9/2001 | Aoki et al. | |

FOREIGN PATENT DOCUMENTS

| EP | 0 593 176 A2 | 4/1994 |
|---|---|---|
| EP | 0 770 395 A1 | 5/1997 |
| JP | H6-510779 | 12/1994 |
| JP | H8-511537 | 12/1996 |
| JP | H9-507234 | 7/1997 |
| WO | WO 93/05800 | 4/1993 |
| WO | WO 94/28922 | 12/1994 |
| WO | WO 94/28923 | 12/1994 |
| WO | WO 95/17904 | 7/1995 |
| WO | WO 95/30431 | 11/1995 |
| WO | WO 95/32738 | 12/1995 |
| WO | WO 97/35604 | 10/1997 |

OTHER PUBLICATIONS

Spinelli et al. Arch. Ophthalmol. 98: 1106-1109, 1980.*
Ashton et al., "A sensitive and useful radioimmunoassay for neurotoxin and its haemagglutinin complex from Clostridium botulinum," Toxicon, 23:235-246 (1985).
Binz et al., "The complete sequence of botulinum neurotoxin type A and comparison with other clostridial neurotoxins," J Biol Chem., 265:9153-58 (1990).
Dasgupta et al., "Cation-exchange chromatography of *Clostridium botulinum* type A toxin on amberlite IRC-50 resin at pH 5.55," Biochim. Biophys. Acta 168:522-531 (1968).
Dasgupta et al., "Chromatographic isolation of hemagglutinin-free neurotoxin from crystalline toxin of *Clostridium botulinum* type A," Biochim. Biophys. Acta, 147:603-605 (1967).
Dasgupta et al., "Purification and amino acid composition of type A botulinum neurotoxin," Toxicon, 22:415-424 (1984).
East et al., "Cloning and Sequencing . . . ," System Appl. Microbiol., 17:306-312, 1994.
East et al., "Conserved structure of genes encoding components of botulinum neurotoxin complex M and the sequence of the gene coding for the nontoxic component in nonproteolytic *Clostridium botulinum* type F," Curr. Microbiol., 29:69-77 (1994).
Fu et al., "A protease-resistant novel hemagglutinin purified from type A *Clostridium botulinum*," J. Protein Chem., 17:53-60 (1998).
Fu et al., In: 5th Pan American Symposium on Animal Plant and Microbial Toxins, Frederick, MD, Jul. 30 to Aug. 4, Abstract, p. 76, 1995.
Fu, Dissertation Abstracts International, vol. 58, No. 9B, abstract (1997).
Fujita et al., "Molecular characterization of two forms of nontoxic-nonhemagglutinin components of *Clostridium botulinum* type A progenitor toxins", FEBS Letters, vol. 376:41-44 (1995).
Göschel et al., Botulinum A Toxin Therapy: Neutralizing and Non-neutralizing Antibodies-Therapeutic Consequences, Experimental Neurology, vol. 147:96-102 (1997).
Hambleton, "Clostridium botulinum toxins: a general review of involvement in disease, structure, mode of action and preparation for clinical use," J. Neurol, 239:16-20, abstract (1992).
Inoue et al., "Molecular composition of *Clostridium botulinum* type A progenitor toxins," Infect. Immun., 64:1589-94 (1996).
LaPenotiere et al., Toxicon 33: 1383-1386, 1995.
Lindo et al., In: Program and Abstracts of the 11th Symposium of the Protein Society, Boston, MA, Jul. 12-16, Cambridge University press, abstract 267-S, p. 100 (1997).
Men et al., Vaccine 14: 1442-1450, 1996.
Sakaguchi, "*Clostridium botulinum* toxins," Pharmac. Ther., 19:165-194 (1983).
Sambrook et al., Molecular Cloning—A Laboratory Manual, Second Edition, Cold Spring Harbor, pp. 17.2-17.44 (1989).

(Continued)

Primary Examiner — S. Devi

(74) *Attorney, Agent, or Firm* — Sunstein Kann Murphy & Timbers LLP

(57) ABSTRACT

An isolated, biologically active 33 kDa hemagglutinin purified from the type A *Clostridium botulinum* neurotoxin complex and its uses are described.

16 Claims, 9 Drawing Sheets

(56) References Cited

OTHER PUBLICATIONS

Sharma et al., "A Direct Binding . . . ," Abstract of the 97th General Meeting of the American Society for Microbiology p. 440, p. 23, 1997.

Sharma et al., "*Clostridium Botulinum* . . . ," Universtiy of Massachusetts Dartmouth Third Annual Sigma Xi Research Exhibit, Apr. 1997.

Sharma et al., "Hemagglutinin binding mediated protection of botulinum neurotoxin from proteolysis," J. Nat. Toxins, 7:239-53 (1998).

Sharma et al., "Immunological Properties . . . ," Protein Science Ninth Symposium Program & Abstracts p. 110, 269-S, 7:8-12, 1995.

Sharma et al., In: Abstracts of the 11th Symposium of the Protein Society, Boston, MA, Jul. 12-16, abstract 262-M, p. 99, 1997.

Sharma et al., J. Protein Chem., 18:9-38, January, abstract (1999).

Shone et al., "Monoclonal antibody-based immunoassay for type A *Clostridium botulinum* toxin is comparable to the mouse bioassay," Appl. Environ. Microbiol, 50:63-67 (1985).

Shukla et al., In: Abstracts of the 97th General Meeting of the Aerican Society of Microbiology, Miami Beach, May 4-8, abstract K-127, p. 363 (1997).

Simpson et al., "Isolation and characterization of the Botulinum neurotoxins," Meth. Enzymol, 165:76-85 (1988).

Sing et al., "Botulinum versus tetanus neurotoxins: why is botulinum neurotoxin but not tetanus neurotoxin a food poison?", Toxicon, 33:1541-547 (1995).

Singh et al., "Gene probe-based detection of type E botulinum neurotoxin binding protein using polymerase chain reaction," Toxicon, 34:737-42 (1996).

Singh et al., "Immunochemical characterization of type A botulinum neurotoxin in its purified and complexed forms," Toxicon, 34:267-275 (1996).

Singh et al., "Molecular Composition . . . ," 2nd International Meeting of the Molecular Genetics & Pathogenesis of Clostridia p. 40, 6:22-25, 1997.

Singh et al., "Physicochemical and immunological characterization of the type E botulinum neurotoxin binding protein purified from *Clostridium botulinum*" J. Protein Chem., 14:7-18 (1995).

Somers et al., "*Clostridium botulinum* types A, B, C1, and E produce proteins with or without hemagglutinating activity: do they share common amino acid sequences and genes?" J. Protein Chem., 10:415-425, 1991.

Sugiyama et al., Proc. Soc. Exper. Boil. Med. 147: 589-591, 1974.

Tse et al., "Preparation and characterisation of homogeneous neurotoxin type A from *Clostridium botulinum*. Its inhibitory action on neuronal release of acetylcholine in the absence and presence of beta-bungarotoxin," European J. Biochem., 122:493-500 (1982).

Tsuzuki et al., "Cloning and complete nucleotide sequence of the gene for the main component of hemagglutinin produced by *Clostridium botulinum* type C," Infect. Immun., 58:3173-77 (1990).

Vinogradova et al., Biokhimiia, "Preparation of neurotoxin and hemagglutinin from *Clostridium botulinum* A and characterization of its neurotoxin]," Biokhimiia, 48:788-796 (1983).

Walker, B. In: Peptide Antigens: A Practical Approach. (Ed) Wisdon GB. IRL Press, Oxford University Press, New York, pp. 27-81 (1994).

Canadian Office Action; Application No. 2,319,113; mailed Mar. 25, 2009; 3 pages.

European Office Action; Application No. 99 903 359.0-2402; mailed Apr. 9, 2008; 6 pages.

European Office Action; Application No. 99 903 359.0-2402; mailed Aug. 16, 2006; 9 pages.

Japanese Decision on Rejection; Application No. 2000-528306; issued Jan. 18, 2010; 2 pages.

Japanese Office Action; Application No: 2000-528306; issued Mar. 4, 2009; 10 pages.

* cited by examiner

FIG. 8

Met Glu His Tyr Ser Val Ile Gln Asn Ser Leu Asn Asp Lys Ile Val
Thr Ile Ser Cys Lys Ala Asp Thr Asn Leu Phe Tyr Gln Val Ala
Gly Asn Val Ser Leu Phe Gln Gln Thr Arg Asn Tyr Leu Glu Arg Trp
Arg Leu Ile Tyr Asp Ser Asn Lys Thr Ala Ala Tyr Lys Ile Lys Ser Met
Asp Ile His Asn Thr Gln Gly Asn Leu Val Leu Thr Trp Asn Ala Pro Thr His
Asn Ile Ser Asn Thr Gln Ile Asp Ser Asn Ala Gln Gln Tyr Trp Leu
Leu Leu Lys Asp Gly Ile Asn Tyr Ala Asp Ile Ile Ala Ser Tyr Lys
Asn Pro Asn Leu Val Leu Tyr Ala Phe Thr Val Ala Arg Asn Leu Lys
Leu Ser Thr Leu Asn Asn Ser Asn Tyr Ile Thr Ile Phe Ile Glu Asp
Tyr Ile Ile Ser Asp Leu Asn Asn Phe Thr Ile Lys Ile Ser Pro Ile
Leu Asp Ser Lys Val Val Gln Gln Thr Cys Lys Asp Val Thr Asn Leu Asn
Val Asn Leu Tyr Thr Asp Tyr Gly Arg Val Asp Gln Lys Trp Thr Ile
Arg Tyr Asn Glu Glu Trp Ala Ala Tyr Gln Asn Phe Phe Asn Thr Ile Leu
Ser Asn Gly Val Leu Thr Trp Ile Phe Gln Phe Ser Ala Gly Ala Asn Thr Val Arg
Val Ser Ser Ser Asn Asp Gln Ala Asn Gln Ala Gln Tyr Ala Gln Tyr Trp Leu Ile
Asn Pro Val Ser Asp Thr Asp Glu Leu Phe Tyr Thr Thr Ile Thr Thr Asn Leu Arg
Asp Thr Thr Lys Ala Leu Asp Leu Tyr Gly Gln Gly Asp Thr Ala Asn Gly
Thr Ala Ile Gln Val Phe Asn Tyr His Gly Asp Asn Gln Lys Trp
Asn Ile Arg Asn Pro (SEQ ID NO:1)

FIG. 9

SEQUENCE LISTING

```
<160> NUMBER OF SEQ ID NOS: 3

<210> SEQ ID NO 1
<211> LENGTH: 293
<212> TYPE: PRT
<213> ORGANISM: Clostridium botulinum

<400> SEQUENCE: 1

Met Glu His Tyr Ser Val Ile Gln Asn Ser Leu Asn Asp Lys Ile Val
 1               5                  10                  15

Thr Ile Ser Cys Lys Ala Asp Thr Asn Leu Phe Tyr Gln Val Ala
                20                  25                  30

Gly Asn Val Ser Leu Phe Gln Gln Thr Arg Asn Tyr Leu Glu Arg Trp
                35                  40                  45

Arg Leu Ile Tyr Asp Ser Asn Lys Ala Ala Tyr Lys Ile Lys Ser Met
     50                  55                  60

Asp Ile His Asn Thr Asn Leu Val Leu Thr Trp Asn Ala Pro Thr His
 65                  70                  75                  80

Asn Ile Ser Thr Gln Gln Asp Ser Asn Ala Asp Asn Gln Tyr Trp Leu
                 85                  90                  95

Leu Leu Lys Asp Ile Gly Asn Asn Ser Phe Ile Ile Ala Ser Tyr Lys
                100                 105                 110

Asn Pro Asn Leu Val Leu Tyr Ala Asp Thr Val Ala Arg Asn Leu Lys
             115                 120                 125

Leu Ser Thr Leu Asn Asn Ser Asn Tyr Ile Lys Phe Ile Ile Glu Asp
         130                 135                 140

Tyr Ile Ile Ser Asp Leu Asn Asn Phe Thr Cys Lys Ile Ser Pro Ile
145                 150                 155                 160

Leu Asp Leu Asn Lys Val Val Gln Gln Val Asp Val Thr Asn Leu Asn
                165                 170                 175

Val Asn Leu Tyr Thr Trp Asp Tyr Gly Arg Asn Gln Lys Trp Thr Ile
             180                 185                 190

Arg Tyr Asn Glu Glu Lys Ala Ala Tyr Gln Phe Phe Asn Thr Ile Leu
         195                 200                 205

Ser Asn Gly Val Leu Thr Trp Ile Phe Ser Asn Gly Asn Thr Val Arg
     210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255

Asp Thr Thr Lys Ala Leu Asp Leu Tyr Gly Gly Gln Thr Ala Asn Gly
             260                 265                 270
```

```
Thr Ala Ile Gln Val Phe Asn Tyr His Gly Asp Asp Asn Gln Lys Trp
        275                 280                 285

Asn Ile Arg Asn Pro
        290

<210> SEQ ID NO 2
<211> LENGTH: 10
<212> TYPE: PRT
<213> ORGANISM: Clostridium botulinum

<400> SEQUENCE: 2

Val Ile Gln Asn Ser Leu Asn Asp Lys Ile
1               5                   10

<210> SEQ ID NO 3
<211> LENGTH: 15
<212> TYPE: PRT
<213> ORGANISM: Clostridium botulinum

<400> SEQUENCE: 3

Met Glu His Tyr Ser Val Ile Gln Asn Ser Leu Asn Lys Asp Ile
1               5                   10                  15
```

BIOLOGICALLY ACTIVE HEMAGGLUTININ FROM TYPE A *CLOSTRIDIUM BOTULINUM* AND METHODS OF USE

CROSS-REFERENCE TO RELATED APPLICATIONS

This application is a continuation of U.S. application Ser. No. 11/286,515, filed on Nov. 22, 2005, now U.S. Pat. No. 7,531,183, which is a continuation of U.S. application Ser. No. 09/546,727, filed on Apr. 11, 2000, now U.S. Pat. No. 6,994,859, which is a continuation of U.S. application Ser. No. 09/013,411, filed on Jan. 26, 1998, now abandoned, which are incorporated herein by reference in their entirety.

STATEMENT AS TO FEDERALLY SPONSORED RESEARCH

This invention was made with Government grants from the Naval Research Laboratory/United States Army Edgewood Research, Development, and Engineering Center (N00014-92-K-2007), the U.S. Department of Agriculture (94-37201-1167), and the National Institutes of Health (NS33740). The Government may have certain rights in the invention.

BACKGROUND OF THE INVENTION

The invention relates to the isolation of a biologically active hemagglutinin protein from the *Clostridium botulinum* type A neurotoxin complex.

Botulinum neurotoxins (BoNTs) are extremely potent proteins with a mouse lethal dose of 0.3 ng/kg. Seven serotypes (A-G) of BoNTs are produced by different strains of *Clostridium botulinum*. In addition, certain nonbotulinum species of *Clostridium*, such as *C. butyricum* and *C. baratii*, have been shown to produce the toxins. The neurotoxin is a protein of about 150 kDa and consists of two polypeptide chains (a 50 kDa light chain and a 100 kDa heavy chain), which are linked together via a disulfide bond.

BoNTs are often produced by bacteria under anaerobic conditions in improperly stored or processed foods. Ingestion of the contaminated food can cause the flaccid muscle paralysis known as botulism.

The mechanism by which BoNTs cause botulism has been well studied. After ingestion, the neurotoxin is translocated across the intestinal mucosa, gaining access to neuromuscular junctions. At affected junctions, the neurotoxin is internalized by neurons via endocytosis. Inside the cell, the toxin's protease activity degrades specific vesicular and plasma membrane proteins, disrupting neurotransmitter release from the neuron. Thus, the patient experiences paralysis due to an inability to release neurotransmitters from the presynaptic surface. This process is reviewed in Sakaguchi, *Pharmac. Ther.*, 19:165-194 (1983).

SUMMARY OF THE INVENTION

The invention is based on the isolation of biologically active, protease resistant hemagglutinin from the type A *Clostridium botulinum* neurotoxin complex. This protein is estimated to have a molecular weight of 33 kDa by sodium dodecylsulfate polyacrylamide gel electrophoresis (SDS-PAGE), and therefore this protein and corresponding polypeptides are referred to herein as "Hn-33." Hn-33 is "biologically active" if the polypeptide exhibits hemagglutinin activity in a hemagglutination assay (described below).

The isolated, biologically active Hn-33 can be used in oral vaccines to protect the antigen from degradation in the gastrointestinal (GI) tract or, alternatively, in a pharmaceutical composition suitable for injection into a muscle or its surrounding tissue to alleviate abnormal firing of neuromuscular junctions.

In general, the invention features a composition including an isolated, biologically active Hn-33 from type A *Clostridium botulinum* and at least one neurotoxin, e.g., type A *botulinum* neurotoxin, type E *botulinum* neurotoxin, or tetanus toxin. The composition can further include a pharmaceutical carrier suitable for administration to an animal. The pharmaceutical carrier can be an adjuvant, or a separate adjuvant can be added. The pharmaceutical carrier can include any one or more of, e.g., polysorbates, ethanol, starch, and glycerin.

In another aspect, the invention features an isolated, biologically active Hn-33 polypeptide of type A *Clostridium botulinum*. An isolated Hn-33 polypeptide is one that has been separated from components which naturally accompany it. Typically, the protein is isolated when it is at least 60%, by weight, free from the proteins and naturally-occurring organic molecules with which it is naturally associated. Preferably, the preparation is at least 75%, more preferably at least 90%, and most preferably at least 99%, by weight, Hn-33. Such an isolated Hn-33 can be obtained, for example, by fractionating a type A *C. botulinum* culture, by expression of a nucleic acid encoding Hn-33, or by chemically synthesizing the protein. Purity can be measured by any appropriate method, e.g., column chromatography or gel filtration. Biologically active Hn-33 must be isolated in a way to ensure that the resulting polypeptide maintains hemagglutinin activity.

The Hn-33 polypeptide of the invention need not be a full-length polypeptide nor be identical to the wild-type amino acid sequence. Hn-33 polypeptides containing truncations, deletions, or amino acid substitutions are included, as long as the polypeptide or protein is biologically active as described herein. As used herein, the terms "polypeptide" and "protein" are used interchangeably.

The invention also features a method of eliciting an immune response against a neurotoxin, e.g., type A *botulinum* neurotoxin, type E *botulinum* neurotoxin, or tetanus toxin, in an animal, e.g., a human or a wild or domesticated animal such as a dog, cat, bird, cow, pig, or horse, by administering to the animal, e.g., orally, an amount of a composition effective to elicit an immune response against the neurotoxin, the composition including an isolated, biologically active Hn-33 of type A *Clostridium botulinum* and a neurotoxin. The composition can further include an adjuvant and/or a biodegradable polymer that enables slow release of the Hn-33/toxin composition.

In another aspect, the invention features a method of treating or preventing a neuromuscular condition, e.g., a smooth muscle spasm or a skeletal muscle spasm, in an animal, e.g., a human, by administering to the animal an amount of a composition effective to treat or prevent the neuromuscular condition, the composition including an isolated, biologically active Hn-33 of type A *Clostridium botulinum* and a neurotoxin, e.g., type A *botulinum* neurotoxin, type E *botulinum* neurotoxin, or tetanus toxin. For example, the composition can be injected into a muscle in need of treatment or a tissue surrounding the muscle. The composition can further include a polymer that enables slow release of the neurotoxin. The method also can be used to treat certain neuromuscular headaches and cerebral palsy.

A "neurotoxin" (or "toxin") is any active, attenuated, or inactive polypeptide that inhibits neurotransmitter release from a presynaptic membrane of a neuromuscular junction. When used in a vaccine composition, the neurotoxin is preferably inactive or at least attenuated. When used in a therapeutic composition to treat abnormal firing of a neuromuscular junction, the neurotoxin is preferably fully active. Suitable neurotoxins for use in the compositions and methods of this invention include, for example, type A *botulinum* neurotoxin, type E *botulinum* neurotoxin, and tetanus toxin.

An "adjuvant" is a substance that is incorporated into or is administered simultaneously with the vaccine compositions of the invention. Adjuvants increase the duration or level of the immune response in the animal after administration of the polypeptide or peptide mimetic. An adjuvant can also facilitate delivery of the polypeptide or peptide mimetic into the animal or into specific tissues, cells, or locations throughout the body of the animal. Examples of adjuvants include, but are not limited to, incomplete Freund's, complete Freund's, and alum; and can contain squalene (e.g., MF59, Chiron Corp, Emeryville, Calif.), monophospholipid A (e.g., Detox™, Ribi ImmunoChem Research, Inc., Hamilton, Mont.), saponins (QS-21, Cambridge Biotech, Cambridge, Mass.), non-ionic surfactants (NISV, Proteus, Cheshire, United Kingdom), tocols (U.S. Pat. No. 5,667,784), biodegradable-biocompatible poly-D,L-lactide-co-glycolide (U.S. Pat. No. 5,417,986), immune-stimulating complexes (IS-COMs), and/or liposomes.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 8 is a bar graph showing cleavage of SNAP-25 substrate by *botulinum* neurotoxins.

FIG. 9 is the amino acid sequence of the full-length Hn-33 polypeptide.

DETAILED DESCRIPTION

Figure 1:
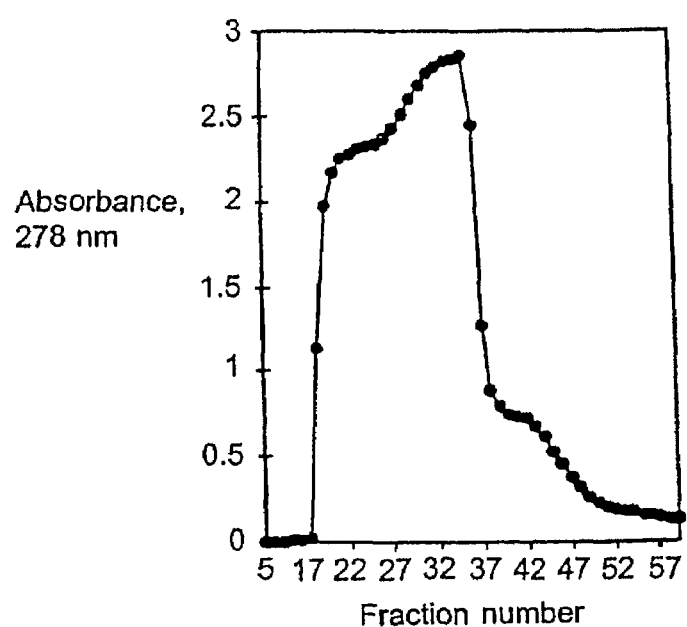
FIGS. 1, 2, 4, and 7 are elution profiles from chromatography columns. The profile in FIG. 1 is a DEAE-SEPHADEX™ A-50 column separation of a crude type A *C. botulinum* extract. The profile in FIG. 2 is a SEPHADEX™ G-100 column separation of a crude type A *botulinum* neurotoxin complex. The profiles in FIG. 4 are a SEPHADEX™ G-200 column separation of isolated, biologically active Hn-33 (in black) and standard proteins (in gray). The profile in FIG. 7 is a SEPHADEX™ G-200 column separation of an Hn-33/type A neurotoxin composition.

The invention relates to isolated, biologically active, protease resistant hemagglutinin polypeptides from the type A *Clostridium botulinum* neurotoxin complex referred to herein as Hn-33. Hn-33 can be used in vaccines, e.g., oral vaccines, to protect the antigen from degradation in the GI tract, or in a pharmaceutical composition suitable for injection into a muscle or its surrounding tissue to alleviate abnormal excitation of a neuromuscular junction.

I. Production and Isolation of Biologically Active Hn-33

A. Production

Biologically active Hn-33-derived proteins and polypeptides include any protein or polypeptide sharing a functional characteristic with biologically active, wild type Hn-33. Such functionally related, biologically active Hn-33 polypeptides include polypeptides having additions or substitutions of amino acid residues within the Hn-33 amino acid sequence compared to the wild type Hn-33 sequence (see FIG. 9 and East et al., *System. Appl. Microbiol.* 17:306-312, 1994; SEQ ID NO:1). Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Biologically active Hn-33 variants with altered amino acid sequences can be created by making random mutations to Hn-33 DNA (which has been described in East et al., *Curr. Microbiol.*, 29:69-77, 1994) using random mutagenesis techniques well known to those skilled in the art, and isolating the polypeptide in a way that yields biologically active Hn-33. Alternatively, site-directed mutations of the Hn-33 coding sequence can be engineered using techniques also well-known to those skilled in the art.

To design variant biologically active Hn-33 polypeptides, it is useful to distinguish between conserved positions and variable positions. To produce variants with functions most similar to wild type, biologically active Hn-33, it is preferable that conserved residues are not altered. Moreover, alteration of non-conserved residues are preferably conservative alterations, e.g., a basic amino acid is replaced by a different basic amino acid. To produce altered function variants, it is preferable to make non-conservative changes at variable and/or conserved positions. Deletions at conserved and variable positions can also be used to create variants.

Other mutations to the Hn-33 coding sequence can be made to generate biologically active Hn-33 polypeptides that are better suited for expression, e.g., for scaled up production, in a selected host cell.

Biologically active Hn-33 polypeptides test positive in a hemagglutination assay (described below), and have a specified function (i.e., protects a therapeutic protein drug from degradation). In determining whether a particular biologically active Hn-33 polypeptide or variant thereof is functional, one can use any assay techniques disclosed herein or techniques disclosed in references incorporated herein. Biologically active Hn-33 polypeptides and variants can have 40%, 60%, 75%, 95%, 100%, or an even higher percentage, of the activity of the full-length, biologically active, wild type Hn-33 (i.e., a variant can have higher activity than the wild type Hn-33). Such comparisons are generally based on equal concentrations of the molecules being compared. The comparison can also be based on the amount of protein or polypeptide required to reach 50% of the maximal activity obtainable.

In general, biologically active Hn-33 can be isolated from its natural host, type A *Clostridium botulinum* bacteria (A.T.C.C. Nos. 3502, 17862, 19397, 25763, and 51385). Alternatively, biologically active Hn-33 polypeptides according to the invention can be produced by transformation (transfection, transduction, or infection) of a host cell with an Hn-33-encoding DNA fragment in a suitable expression vehicle. Suitable expression vehicles include plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LACSWITCH™ Inducible Expression System (Stratagene; LaJolla, Calif.).

Those skilled in the field of molecular biology will understand that any of a wide variety of expression systems can be used to provide the recombinant protein. The precise host cell used is not critical to the invention.

Proteins and polypeptides can also be produced by plant cells. For plant cells, viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Manassas, Va.; also, see, e.g., Ausubel et al., *Current Protocols in Molecular Biology*, John Wiley & Sons, New York, 1994). The methods of transformation or transfection and the choice of expression vehicle will depend on the host system selected. Transformation and transfection methods are described, e.g., in Ausubel et al. (*Current Protocols in Molecular Biology*, John Wiley & Sons, New York, 1994); expression vehicles may be chosen from those provided, e.g., in *Cloning Vectors: A Laboratory Manual* (P. H. Pouwels et al., 1985, Supp., 1987).

The host cells harboring the expression vehicle can be cultured in conventional nutrient media adapted as need for activation or repression of a chosen gene, selection of transformants, or amplification of a chosen gene.

Specific initiation signals may be required for efficient translation of inserted nucleic acid sequences. These signals include the ATG initiation codon and adjacent sequences. In cases where an entire native biologically active Hn-33 gene, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription or translation enhancer elements, (e.g., ones disclosed in Bittner et al., *Methods in Enzymol.*, 153:516, 1987).

Preferred polypeptides are those which are soluble under normal physiological conditions. Also within the invention are fusion proteins in which a portion (e.g., one or more domains) of biologically active Hn-33 is fused to an unrelated protein or polypeptide (i.e., a fusion partner) to create a fusion protein. The fusion partner can be a moiety selected to facilitate purification, detection, or solubilization, or to provide some other function. Fusion proteins are generally produced by expressing a hybrid gene in which a nucleotide sequence encoding all or a portion of biologically active Hn-33 is joined in-frame to a nucleotide sequence encoding the fusion partner. For example, the expression vector pUR278 (Ruther et al., *EMBO J.*, 2:1791, 1983), can be used to create lacZ fusion proteins. The pGEX vectors can be used to express foreign polypeptides as fusion proteins containing glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

A fusion protein can be readily purified by utilizing an antibody specific for the fusion protein being expressed. For example, a system described in Janknecht et al., *Proc. Natl. Acad. Sci.* USA., 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers. The same procedure can be used for a bacterial culture, e.g., a type A *Clostridium botulinum* culture.

Alternatively, biologically active Hn-33 or a portion thereof, can be fused to an immunoglobulin Fc domain. Such a fusion protein can be readily purified using an affinity column.

Polypeptides of the invention, particularly short, biologically active Hn-33 fragments, can also be produced by chemical synthesis (e.g., by the methods described in *Solid Phase Peptide Synthesis*, 2nd ed., [1984] The Pierce Chemical Co., Rockford, Ill.).

B. Isolation

Both naturally occurring and recombinant forms of Hn-33 must be isolated and tested for biological activity. Secreted forms can be isolated from the culture media, while non-secreted forms must be isolated from the host cells. Polypeptides can be isolated by affinity chromatography. In one example, an anti-Hn-33 protein antibody (produced as described herein) is attached to a column and used to isolate the biologically active Hn-33 protein. Lysis and fractionation of biologically active Hn-33-harboring cells prior to affinity chromatography can be performed by standard methods (see, e.g., Ausubel et al., supra). Alternatively, a biologically active Hn-33 fusion protein, for example, a biologically active Hn-33-maltose binding protein, a biologically active Hn-33-β-galactosidase, or a biologically active Hn-33-trpE fusion protein, can be constructed and used to isolate biologically active Hn-33 (see, e.g., Ausubel et al., supra; New England Biolabs, Beverly, Mass.).

For example, a *C. botulinum* culture is grown in N—Z amine-based growth medium and the cells harvested. After acid precipitation and centrifugation, the cells are lysed and treated with RNAse A. The cell extracts can be fractionated on a DEAE-SEPHADEX™ A-50 column, and the pooled fractions precipitated with ammonium sulfate. The precipitated proteins are then redissolved and fractionated on a G-100 SEPHADEX™ column to yield isolated, biologically active Hn-33.

Once isolated, the Hn-33 polypeptide can, if desired, be further purified and/or concentrated, as long as further processing does not impair biological activity (as measured in the hemagglutination assay described herein). A variety of methods for purification and concentration are well known in the art (see, e.g., Fisher, *Laboratory Techniques In Biochemistry And Molecular Biology*, eds., Work and Burdon, Elsevier 1980), including ultracentrifugation and/or precipitation (e.g., with ammonium sulfate), microfiltration (e.g., via 0.45 µm cellulose acetate filters), ultrafiltration (e.g., with the use of a sizing membrane and recirculation filtration), gel filtration (e.g., columns filled with SEPHAROSE™ CL-6B, CL-4B, CL-2B, 6B, 4B or 2B, SEPHACRYL™ S-400 or S-300, SUPEROSE™ 6 or ULTROGEL™ A2, A4, or A6; all available from Pharmacia), fast protein liquid chromatography (FPLC), and high performance liquid chromatography (HPLC).

C. Physical Properties

After isolation procedures have been performed, the concentration and purity of biologically active Hn-33 can readily be determined. For example, the polypeptide concentration and yields can be determined by a variation of the Bradford assay, using a reagent sold by BIO-RAD™. The purity can be estimated by, for example, the banding resulting from assaying the protein sample on SDS-PAGE.

Other physical properties of Hn-33 variant proteins can be determined. The molecular weight of the proteins can be estimated by methods well know in the art, such as SDS-PAGE, laser desorption mass spectroscopy, and column chromatography. In addition, the secondary structure can be analyzed by circular dichroism analysis as described in Fu et al., *Appl. Spectrosc.*, 48:1432-1441 (1994).

II. Characterization of Hn-33

A. Biological Activity

Isolated Hn-33 proteins can be assayed for biological activity using the hemagglutination assay as described in DasGupta et al., *Can. J. Microbiol.*, 23:1257-1260 (1977) and Example 2 below. Briefly, washed red blood cells (e.g., 0.05 ml of a 0.5% w/w suspension) are added to a small volume (e.g., 50 µl solution) of a Hn-33 polypeptide sample (e.g., 1 ng/ml to 15 or 20 µg/ml, e.g., 416 ng/ml) in a U-bottom well of a microtiter plate. Hemagglutination activity is observed when the red blood cells clump and thus do not form an annular shape or a dot at the bottom of the well within 30 minutes after adding the Hn-33. An Hn-33 polypeptide is considered biologically active if a concentration of Hn-33 of as low as 300 ng/ml results in hemagglutination in the above assay.

B. Function

An isolated, biologically active Hn-33 polypeptide can be assayed for the percentage of biologically active, wild-type Hn-33 protein function as described in Examples 2 and 6 below. Briefly, the Hn-33 and neurotoxin proteins are mixed in a Hn-33:neurotoxin, by weight, ratio of at least 1. The mixture is dialyzed against a protease digestion buffer for 30 minutes, digested for at least 20 minutes, and subsequently analyzed by SDS-PAGE and standard visualization procedures (e.g., COOMASSIE BLUE™ staining of the gel). The biologically active Hn-33 polypeptide preferably exhibits at least 40, 60, 80, 90, 100 percent, or even a higher percentage, of the protective function of the wild type, biologically active Hn-33 protein.

C. Antibodies

Biologically active Hn-33 polypeptides can be used to generate anti-Hn-33 antibodies, e.g., antibodies that are specific for the biologically active form of the protein. Such biologically active-specific antibodies can be used in diagnostic and therapeutic procedures that require the enhancement, inhibition, or detection of the type A neurotoxin complex.

Biologically active Hn-33 polypeptides (or immunogenic fragments or analogs) can be used to raise antibodies. In general, the biologically active Hn-33 can be coupled to a carrier protein such as KLH (as described in Ausubel et al., supra), mixed with an adjuvant, and injected into a host mammal to produce polyclonal antibodies. These antibodies can be purified by antigen affinity chromatography. Polyclonal antibodies are heterogeneous populations of antibody molecules derived from the sera of the immunized animals.

In particular, various host animals can be immunized by injection with a biologically active Hn-33 protein. Host animals can include rabbits, mice, guinea pigs, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Antibodies include polyclonal antibodies, monoclonal antibodies, humanized or chimeric antibodies, single chain antibodies, Fab fragments, $F(ab')_2$ fragments, and molecules produced using a Fab expression library.

Monoclonal antibodies, which are homogeneous populations of antibodies to a particular antigen, can be prepared using the biologically active Hn-33 polypeptides described above and standard hybridoma technology (see, e.g., Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., In *Monoclonal Antibodies and T Cell Hybridomas*, Elsevier, N.Y., 1981; U.S. Pat. No. 4,376,110; Kosbor et al., *Immunology Today*, 4:72, 1983; Cole et al., *Proc. Natl. Acad. Sci.* USA, 80:2026, 1983; Cole et al., *Monoclonal Antibodies and Cancer Therapy*, Alan R. Liss, Inc., pp. 77-96, 1983; and Ausubel et al., supra). Such antibodies can be of any immunoglobulin class including IgG, IgM, IgE, IgA, IgD and any subclass thereof. The hybridoma producing the Mab of this invention may be cultivated in vitro or in vivo. The ability to produce high titers of mAbs in vivo makes this the presently preferred method of production.

Once produced, polyclonal or monoclonal antibodies are tested for specific biologically active Hn-33 recognition by Western blot or immunoprecipitation analysis by standard methods, e.g., as described in Ausubel et al., supra. Antibodies that specifically recognize and bind to biologically active Hn-33 can be used, e.g., in an immunoassay to monitor the level of biologically active Hn-33 or type A neurotoxin produced by a *Clostridium botulinum*-infected mammal (for example, to determine the amount or subcellular location of biologically active Hn-33).

Antibodies of the invention can be produced using fragments of the biologically active Hn-33 protein which lie outside highly conserved regions and appear likely to be antigenic, e.g., based on criteria such as high frequency of charged residues. Such fragments can include a discontinuous, biologically active-specific epitope as well. In one specific example, such fragments are generated by standard techniques of PCR and are then cloned into the pGEX expression vector (Ausubel et al., supra). Fusion proteins are expressed in *E. coli* and purified using a glutathione agarose affinity matrix as described in Ausubel et al., supra.

In some cases it may be desirable to minimize the potential problems of low affinity or specificity of antisera. In such circumstances, two or three separate fusion proteins can be generated, and each fusion can be injected into at least two rabbits. Antisera can be raised by injections in a series, preferably including at least three booster injections.

Antisera is also checked for its ability to immunoprecipitate recombinant biologically active Hn-33 polypeptides or control proteins, such as glucocorticoid receptor, CAT, or luciferase.

The antibodies can be used, for example, to detect biologically active Hn-33 in a biological sample as part of a diagnostic assay, and also to evaluate the effectiveness of medical treatments by other therapeutic approaches. Antibodies also can be used in a screening assay to measure the effect of a candidate compound on localization of biologically active Hn-33.

In addition, techniques developed for the production of "chimeric antibodies" (Morrison et al., *Proc. Natl. Acad. Sci. USA*, 81:6851, 1984; Neuberger et al., *Nature*, 312:604, 1984; Takeda et al., *Nature*, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine Mab and a human immunoglobulin constant region.

Alternatively, techniques described for the production of single chain antibodies (U.S. Pat. Nos. 4,946,778, 4,946,778, and 4,704,692) can be adapted to produce single chain antibodies against a biologically active Hn-33. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include, but are not limited to, F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Antibodies to the biologically active Hn-33 can, in turn, be used to generate anti-idiotype antibodies that resemble a portion of biologically active Hn-33, using techniques well known to those skilled in the art (see, e.g., Greenspan et al., *FASEB J.*, 7:437, 1993; Nissinoff, *J. Immunol.*, 147:2429 1991). For example, antibodies that bind to biologically active Hn-33 and competitively inhibit the binding of a ligand of biologically active Hn-33 (e.g., o-nitropheny-β-D-galactoside or isopropyl-β-D-thiogalactoside) can be used to generate anti-idiotypes that resemble a ligand binding domain of biologically active Hn-33 and, therefore, bind and neutralize a ligand of biologically active Hn-33. Such neutralizing anti-idiotypic antibodies or Fab fragments of such anti-idiotypic antibodies can be used in therapeutic regimens.

D. Protease Resistance

Biologically active Hn-33 or a complex containing biologically active Hn-33 has now been shown to be resistant to a variety of proteases. This protease resistance can be tested by methods well known in the art. For instance, a pre-determined amount of Hn-33 or Hn-33 complex (e.g., 10 μg to 100 mg) is mixed with a solution containing a selected protease (e.g., trypsin, chymotrypsin, subtilisin, pepsin, cathepsin B, ancord, asparaginase, bromelain, clostraipain, ficin, kallikarein, or papain) at a pre-determined w/w ratio (e.g., 25:1 to 1000:1 Hn-33:protease ratio) for a pre-determined length of time (e.g., 10 minutes to 24 hours). The digestion is carried out at a temperature (e.g., room temperature or 37° C.) and pH (e.g., 2.0 to 8.0) suitable for each protease and can be stopped by adding to the digest any number of protease inhibitors known in the art (e.g., PMSF).

E. Effect on Neurotoxin Protease Activity

Biologically active Hn-33 can have an effect on the protease activity of a number of neurotoxins (e.g., *botulinum* type A neurotoxin, *botulinum* type E neurotoxin, and tetanus toxin). The protease activity of a neurotoxin complex containing an isolated, biologically active Hn-33 can be measured using any suitable substrate (e.g., glutathione-S-transferase-SNAP-25 fusion protein, VAMP-2, Syntaxin—for type C1 *botulinum* neurotoxin only, or Cellubrevin) in which at least one of the cleavage products (e.g., SNAP-25) is detectable (e.g., by Western blotting using an antibody which binds to the SNAP-25 C-terminus). Additional agents (e.g., sugars or detergents such as SDS) can be added to the digestion to test the additional agent's effect on neurotoxin protease activity.

III. Preparation of Pharmaceutical Compositions Containing Biologically Active Hn-33

Since biologically active Hn-33 protects *botulinum* neurotoxin type A from proteolytic degradation (shown in Example 6 below), Hn-33 is useful as a carrier protein in the preparation of pharmaceutical compositions such as vaccines or therapeutics.

The isolation and purification of Hn-33 and type A and type E *botulinum* neurotoxins are described below. Tetanus toxin can be isolated and purified according to the method described in Schiavo et al., *Methods Enzymol.* 248:643-652 (1995).

A. Vaccine Compositions

The invention includes vaccine compositions (e.g., oral vaccines) containing at least one neurotoxin (e.g., type A *botulinum* neurotoxin, type E *botulinum* neurotoxin, or tetanus toxin), which can be active or inactive, biologically active Hn-33 (or a biologically active immunogenic fragment or derivative thereof), and, optionally, a pharmaceutically acceptable carrier, such as the diluents phosphate buffered saline or a bicarbonate solution (e.g., 0.24 M NaHCO$_3$). The carriers used in the composition are selected on the basis of the mode and route of administration, and standard pharmaceutical practice. Suitable pharmaceutical carriers and diluents, as well as pharmaceutical necessities for their use, are described in Remington's Pharmaceutical Sciences. An adjuvant, e.g., a cholera toxin, *Escherichia coli* heat-labile enterotoxin (LT), liposome, or immune-stimulating complex (IS-COM), can also be included in the new vaccine composition.

Skilled artisans can obtain further guidance in the preparation of a neurotoxin vaccine in Singh et al. (*Toxicon.*, 27:403-410, 1990). Briefly, approximately 0.1 to 2 mg of neurotoxin (e.g., *botulinum* type A neurotoxin or tetanus toxin, or attenuated variants thereof) and 0.1 to 2 mg of biologically active Hn-33 (e.g., the Hn-33:neurotoxin ratio, by weight, can be 1:1 to 20:1) are added to a physiological buffer (e.g., buffers at pH 4-7.5), and are incubated (e.g., at 4° C. to 30° C.) for a time sufficient to allow the Hn-33 to bind to the neurotoxin (e.g., 5 minutes to 2 hours).

B. Therapeutic Compositions

Any disease or discomfort associated with an exaggerated release of acetylcholine from a presynaptic nerve terminal can be treated with a Hn-33 neurotoxin complex. These diseases are associated with either smooth or skeletal muscle spasms, such as spasmodic torticollis, essential tremor, spasmodic dysphonia, charley horse, strabismus, blepharospasm, oromandibular dystonia, spasms of the sphincters of the cardiovascular, gastrointestinal, or urinary systems, and tardive dyskinesia, which may result from treatment with an antipsychotic drug such as THORAZINE® or HALDOL®.

To formulate the therapeutic compositions, Hn-33 is mixed with a neurotoxin in at least a 1:1, by weight, Hn-33:neurotoxin ratio in a physiological buffer (e.g., phosphate buffered saline) at a suitable temperature (0°-37° C.). The resulting Hn-33/neurotoxin complex can be, for example, lyophilized and resuspended in sterile, deionized water. Appropriate pharmaceutical carriers (e.g., the ones described above) can then be added.

The therapeutic compositions can be formulated as a solution, suspension, suppository, tablet, granules, powder, capsules, ointment, or cream. In the preparation of these compositions, at least one pharmaceutical carrier is to be included. Examples of pharmaceutical carriers include solvent (e.g., water or physiological saline), solubilizing agent (e.g., ethanol, polysorbates, or Cremophor EL®), agent for making isotonicity, preservative, antioxidizing agent, excipient (e.g., lactose, starch, crystalline cellulose, mannitol, maltose, calcium hydrogen phosphate, light silicic acid anhydride, or calcium carbonate), binder (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizer (e.g., lactose, mannitol, maltose, polysorbates, macrogols, or polyoxyethylene hardened castor oils) can be added. If necessary, glycerin, dimethylacetamide, 70% sodium lactate, a surfactant, or a basic substance such as sodium hydroxide, ethylenediamine, ethanolamine, sodium bicarbonate, arginine, meglumine, or trisaminomethane is added. Biodegradable polymers such as poly-D, L-lactide-co-glycolide or polyglycolide can be used as a bulk matrix if slow release of the composition is desired (see e.g., U.S. Pat. Nos. 5,417,986, 4,675,381, and 4,450,150). Pharmaceutical preparations such as solutions, tablets, granules or capsules can be formed with these components. If the composition is administered orally, flavorings and colors can be added.

IV. Administration of Pharmaceuticals Compositions Containing Biologically Active Hn-33

The new vaccine and therapeutic compositions can be administered via any appropriate route, e.g., intravenously, intraarterially, topically by injection, intraperitoneally, intrapleurally, orally, subcutaneously, intramuscularly, sublingually, intraepidermally, or rectally.

A. Vaccines

The amount of vaccine administered will depend, for example, on the particular vaccine antigen, whether an adjuvant is co-administered with the antigen, the type of adjuvant co-administered, the mode and frequency of administration, and the desired effect (e.g., protection or treatment), as can be determined by one skilled in the art. In general, the new vaccine antigens are administered in amounts ranging between 1 µg and 100 mg per adult human dose. If adjuvants are administered with the vaccines, amounts ranging between 1 ng and 1 mg per adult human dose can generally be used. Administration is repeated as necessary, as can be determined by one skilled in the art. For example, a priming dose can be followed by three booster doses at weekly intervals. A booster shot can be given at 8 to 12 weeks after the first immunization, and a second booster can be given at 16 to 20 weeks, using the same formulation. Sera or T-cells can be taken from the individual for testing the immune response elicited by the vaccine against the neurotoxin. Methods of assaying antibodies or cytotoxic T-cells against a specific antigen are well known in the art. Additional boosters can be given as needed. By varying the amount of Hn-33, neurotoxin, or pharmaceutical composition, the immunization protocol can be optimized for eliciting a maximal immune response.

Before administering the above compositions in humans, toxicity and efficacy testing in animals are desirable. In an example of efficacy testing, mice (e.g., Swiss-Webster mice) can be vaccinated via an oral or parenteral route with a composition containing Hn-33 and a neurotoxin (e.g., a tetanus toxin or type A *botulinum* neurotoxin). After the initial vaccination or after optional booster vaccinations, the mice (and corresponding control mice receiving mock vaccinations) are challenged with a $LD_{95}$ dose of the toxin. Efficacy is determined if mice receiving the Hn-33/toxin die at a rate lower than the mock-vaccinated mice. Preferably, the difference in death rates should be statistically significant. Rabbits can be used in the above testing procedure instead of mice.

Alternatively, the new Hn-33/neurotoxin vaccine compositions can be administered as ISCOMs. Protective immunity has been generated in a variety of experimental models of infection, including toxoplasmosis and Epstein-Barr virus-induced tumors, using ISCOMS as the delivery vehicle for antigens (Mowat et al., *Immunology Today*, 12:383-385, 1991). Doses of antigen as low as 1 µg encapsulated in ISCOMs have been found to produce class I mediated cytotoxic T cell responses (Takahashi et al., *Nature*, 344:873-875, 1990). Polypeptides are delivered into cells using ISCOMS in a manner and dosage similar to that described above for liposomes.

B. Therapeutic Compositions

The dose of the Hn-33/neurotoxin complex administered to a patient will depend generally upon the severity of the condition, the age, weight, sex, and general health of the patient, and the potency of the toxin, which is expressed as a multiple of the $LD_{50}$ value for the mouse.

The dosages used in human therapeutic applications are roughly proportional to the mass of muscle in need of treatment. Typically, the dose administered to the patient may be from about 0.01 to about 1,000 units, for example, about 5 to 50 or 100, or 200 to 500 units, depending on the particular use. A unit is defined as the amount of Hn-33/neurotoxin that kills 50% of a group of Swiss-Webster mice (typically a group of 18-20 female mice that weigh on average 20 grams). The dosage is adjusted, either in quantity or frequency, to achieve sufficient reduction in acetylcholine neurotransmitter release to afford relief from the symptoms of the disease or condition being treated.

Physicians, pharmacologists, and other skilled artisans are able to determine the most therapeutically effective treatment regimen, which will vary from patient to patient. The potency of *botulinum* toxin and its duration of action means that doses are administered on an infrequent basis (e.g., one 10-200 unit intramuscular injection, for example, once every four to six months, or once every several weeks) and preferably administered in an implant made from a polymer that allows slow release of the toxin. Skilled artisans are also aware that the treatment regimen must be commensurate with questions of safety and the effects produced by the toxin.

Typically, the Hn-33/neurotoxin complex is suspended in a physiologically acceptable solution, such as normal saline, and is administered by an intramuscular injection. Prior to injection, careful consideration is given to the anatomy of the muscle group, in an attempt to inject the toxin complex into the area with the highest concentration of neuromuscular junctions. If the muscle mass is not very great, the injection can be performed with extremely fine, hollow, teflon-coated needles and guided by electromyography. The position of the needle in the muscle should be confirmed prior to injection of the toxin, and general anesthesia, local anesthesia, or other sedation may be used at the discretion of the attending physician, according to the age and particular needs of a given patient and the number of sites to be injected.

As an example, an adult male patient suffering from tardive dyskinesia resulting from treatment with an antipsychotic drug can be treated with 50-200 units (as defined herein) of Hn-33/*botulinum* neurotoxin complex by direct injection into the facial muscles. Within three days, the symptoms of tardive dyskinesia, i.e., orofacial dyskinesia, athetosis, dystonia, chorea, tics, and facial grimacing are markedly reduced.

Spasticity that occurs secondary to brain ischemia, or traumatic injury of the brain or spinal cord, are similarly amenable to treatment.

In instances where the postsynaptic target is a gland, nerve plexus, or ganglion, rather than a muscle, the Hn-33/neurotoxin complex can be administered to control profuse sweating, lacrimation, and mucous secretion. For example, an adult male patient with excessive unilateral sweating can be treated by administering 0.01 to 50 units (as defined herein) of Hn-33/neurotoxin complex to the gland nerve plexus, ganglion, spinal cord, or central nervous system. Preferably, the nerve plexus or ganglion that malfunctions to produce the excessive sweating is treated directly. Administration of the Hn-33/neurotoxin complex to the spinal cord or brain, while feasible, may cause general weakness.

Other conditions that can be treated include tension headache and pain caused by sporting injuries or arthritic contractions. If necessary, overactive muscles can be identified with electromyography (EMG).

EXAMPLES

The invention will be further described in the following examples, which do not limit the scope of the invention described in the claims.

Example 1

Isolation of Biologically Active Hn-33

*C. botulinum*, Hall strain (obtainable as ATCC No. 3502) was grown in N—Z amine-based growth medium, and the Hn-33 isolated according to the procedures described by DasGupta et al., *Toxicon.*, 22:415-424 (1984) and modified as follows. 32 liters of culture were grown in four-9L PYREX™ carboys at 37° C. without agitation. Cells were harvested after 10 days of growth. After acid precipitation and centrifugation, the cell pellets were extracted and digested with RNAse A. The digested crude extracts were then passed through two DEAE-SEPHADEX™ A-50 columns (2.5×60 cm) with 0.05 M citrate buffer, pH 5.5. The column yielded a major elution peak in the void volume (FIG. 1). The first peak containing the crude *botulinum* neurotoxin complex was pooled from the two columns and precipitated with 0.351 g/ml ammonium sulfate solution.

Figure 2:
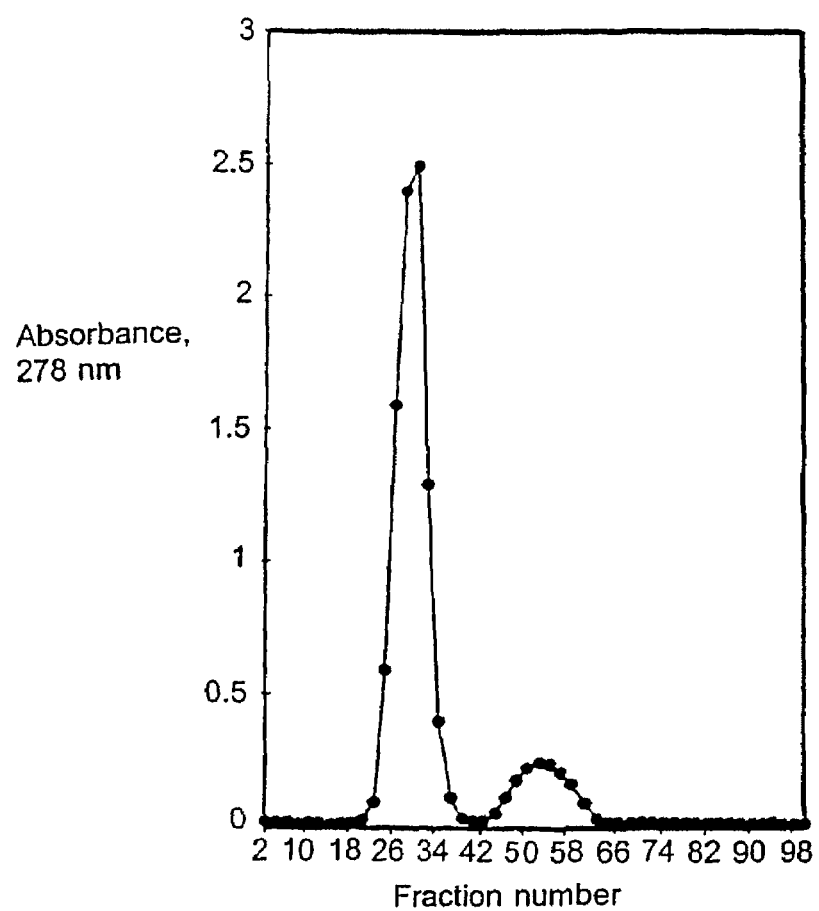

The precipitated proteins were redissolved in 50 mM citrate buffer, pH 5.5, and extensively dialyzed against the same buffer before being loaded onto a G-100 SEPHADEX™ column (2.5×70 cm). Proteins were eluted with the same buffer at a flow rate of 40 ml/hr. The further chromatographic separation of proteins resulted in two peaks (FIG. 2). Both the first and second peaks of the G-100 column elution were collected for further analysis.

To isolate the type A *botulinum* neurotoxin, the crude neurotoxin complex was applied to a second DEAE-A-50 column equilibrated as above and eluted with a 0-0.5 M NaCl gradient buffer. The neurotoxin in the first elution peak was further purified by applying to a SP-C-50 column in 20 mM sodium phosphate buffer (pH 7.9) and eluted with a 0-0.5 M NaCl gradient buffer. The neurotoxin is contained in the second of two elution peaks.

Electrophoretic analysis of the type A *botulinum* complex was carried out on the PHASTSYSTEM™ electrophoresis unit (Pharmacia LKB, Piscataway, N.J.) using a 4-15% gradient acrylamide gel. Electrophoretic data were analyzed with a CCD solid-state video camera (ITTI Inc. St. Petersburg, Fla.) for the molecular weight determination and for the estimation of the relative amount of each band. High molecular weight standards were purchased from Bio-Rad and used for the determination of sample protein molecular weights.

The group of proteins obtained in the first elution band (FIG. 2) has been referred to as the type A *botulinum* neurotoxin complex. The second elution peak of the SEPHADEX™ G-100 column contained a single protein of 33 kDa, otherwise called hemagglutinin-33 or Hn-33.

Estimation of the relative amounts of each component of the type A neurotoxin complex was investigated via densitometry of the SDS-PAGE bands resulting from the first DEAE-A-50 eluted proteins. Under nonreducing conditions, the relative content of the band at 142 kDa was 25%, whereas the band at 120 kDa (corresponding to the neurotoxin) was 7%. Other components of neurotoxin associated proteins (NAPs) were present in significant proportions (54 kDa, 16%; 33 kDa, 25%; 20 kDa, 9%; 17 kDa, 6%; and 14 kDa, 12%). Typically, the yield of purified Hn-33 was about 2% after the SEPHADEX™ G-100 chromatography step.

Concentrations of complex (1.66 mg/ml) and neurotoxin (1.63 mg/ml) were determined according to the extinction coefficients ε (278 nm). The concentration of Hn-33 was determined by the method described in Whitaker et al., *Anal. Biochem.*, 109:156-159 (1980), using the factor $(A_{235}-A_{278})/2.51$. The number 2.51 in the denominator was empirically determined to give the best correlation between absorbance and protein concentration and corrects for the contribution of absorbance by aromatic amino acids at 235 nm.

The molecular weight of Hn-33 was further confirmed by subjecting the isolated protein to matrix-assisted laser desorption mass spectrometry. 15 pmoles of Hn-33 in sinapinic acid was analyzed on a VOYAGER™-RP Biospectrometry Workstation (PerSeptive Biosystem, Boston, Mass.) according to manufacturer's instructions. The spectrometer was operated at an accelerating potential of 30,000 V, and the protein was desorbed by a 336 W intensity laser. The spectrums were obtained with an average of 174 scans. BSA was applied as a standard for assignment of molecular weights, using either singly or doubly charged ions.

Figure 3A:
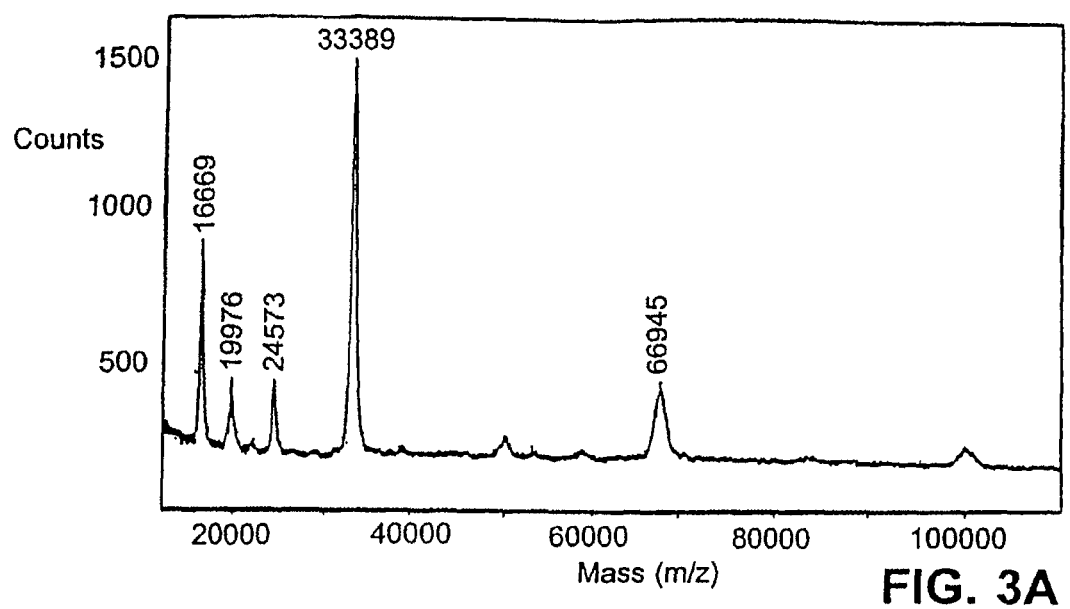
FIGS. 3A and 3B are graphs of a matrix assisted laser desorption mass spectrum of Hn-33. The spectrum in FIG. 3B extends and enlarges the spectrum in FIG. 3A.
Figure 3B:
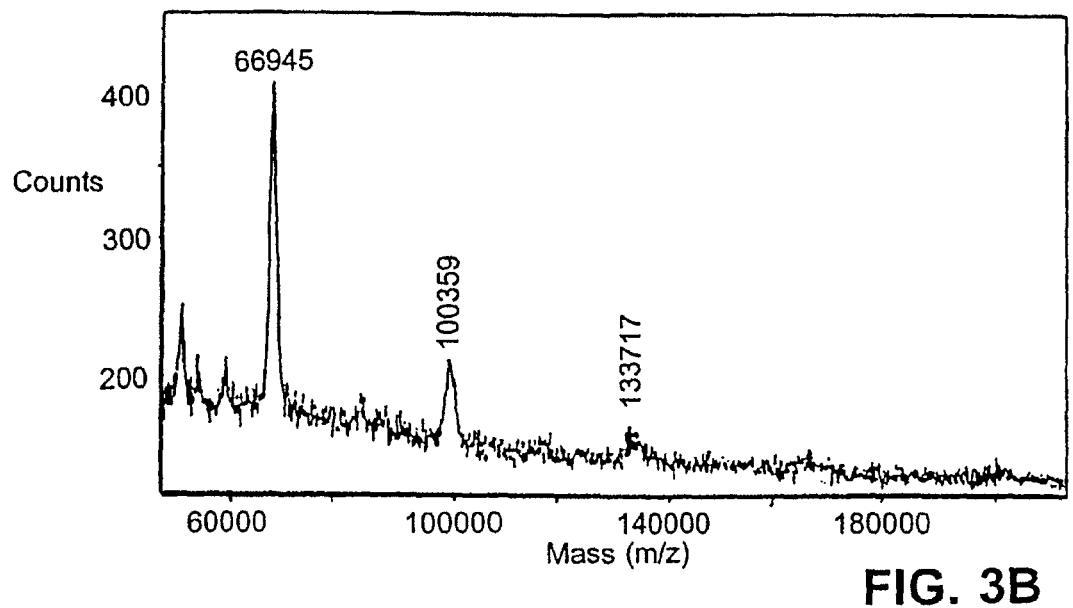

The resulting mass spectrum (FIGS. 3A and 3B) indicated a major band at 33,389 and significant peaks at 66,945 (dimer) and 100,359 (trimer). A weak peak was observed at 133,717 (tetramer) as shown in the expanded graph of FIG. 3B. Masses below 33,389 probably represent higher charged species of Hn-33 or minor impurities.

Figure 4:
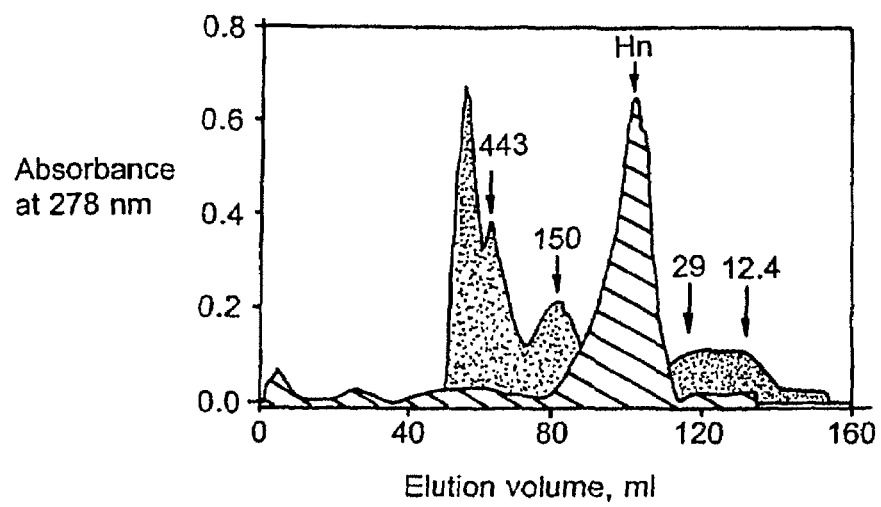

The quaternary structure of isolated, biologically active Hn-33 was further investigated using gel filtration chromatography. Hn-33 at 3.4 mg/ml in 50 mM citrate buffer, pH 5.5, was applied to a SEPHADEX™ G-200 column (1.5×80 cm). Standard elution volumes were obtained with cytochrome C, 12.4 kDa; carbonic anhydrase, 29 kDa; BSA, 66 kDa; alcohol dehydrogenase, 150 kDa; and apoferritin, 443 kDa. A plot of the log of standard MW values vs. standard Rf values (FIG. 4) and comparison with the elution volume of Hn-33 indicated a molecular weight of 69 kDa which is likely to be an Hn-33 dimer. In FIG. 4, the gray shading indicates the elution profile for standard MW proteins, and the black shading indicates elution profile for Hn-33. This assay suggests that a trimeric structure predominates.

Example 2

Measuring Hemagglutination Activity of Isolated Hn-33

Biological activity was determined by the hemagglutination assay as described in DasGupta et al. (1977), supra. Freshly drawn human blood (type A positive) was immediately treated with solution (Gamma Biologicals, Inc., Houston, Tex.) and washed with 0.8% NaCl before use. Washed human erythrocytes (0.05 ml of 0.5% w/w suspension) were added to 0.05 ml of type A *botulinum* toxin, Hn-33, or the neurotoxin complex in 75 mM NaCl in wells of a U-Bottom microtiter plate (Falcon, Becton Dickinson, N.J.). A twofold serial dilution, starting at a concentration of 13.33 µg/ml of neurotoxin, Hn-33, or complex, was used for the assay. Hemagglutination activity was observed when the erythrocytes did not form into an annular shape or a dot in the bottom of the well after 4 hours of incubation.

The purified Hn-33 was effective in eliciting hemagglutination in the above assay at a concentration of 416 ng/ml, which was abolished in the presence of 0.05% SDS. The hemagglutinating activity of the whole neurotoxin complex (including all neurotoxin associated proteins) was observed at a minimum concentration of 52 ng/ml. The purified neurotoxin did not exhibit any hemagglutinating activity at concentrations of 13.33 µg/ml or less.

To determine whether carbohydrates block the hemagglutination activity of Hn-33, 0.5 µg of isolated Hn-33 was mixed with serial dilutions of o-nitrophenyl-β-D-galactoside or isopropyl-β-D-thiogalactoside, two sugars found on the apical surface of GI tract epithelial cells (starting with a 66.7 mM initial concentration), and then subjected to the hemagglutination assay. At a 33 mM carbohydrate concentration, both of the sugars mentioned above inhibited the Hn-33 hemagglutination activity, indicating that Hn-33 binds to these sugars. These results suggest that the new Hn-33/neurotoxin vaccine compositions bind to these sugars on the surface of epithelial cells in the GI tract, facilitating entry of Hn-33/neurotoxin vaccine compositions into the body.

In an attempt to investigate the contribution of different components of the neurotoxin complex to hemagglutination activity, Hn-33-specific antibodies were used to block hemagglutination. Hn-33-specific antibodies were isolated by fractioning a horse anti-type A neurotoxin complex antiserum on a protein-G matrix column as described in Ogert et al., *Anal. Biochem.*, 205:306-312 (1992), followed by fractionation on a Hn-33 affinity column produced by attaching Hn-33 to AFFIGEL™ 15 matrix (Bio-Rad, Hercules, Calif.). After applying the IgG fraction on the AFFIGEL™ column, the column was washed with 0.15 M sodium phosphate buffer, pH 7.0, and eluted with 0.2 M glycine.HCl.

The specificity of the Hn-33 antibodies was confirmed by a Western blot of type A neurotoxin complex proteins. The neurotoxin complex was resolved on a 12.5% SDS-polyacrylamide gel (0.75 mm thick, 8×9 cm minigel) using a Mini-PROTEAN II® electrophoresis cell (Bio-Rad) under reducing conditions (2-mercaptoethanol added). Protein bands were then transferred to a nitrocellulose membrane by transblotting them using a Mini Trans-Blot electrophoretic transfer cell (Bio-Rad) according to the procedure described in Towbin et al., *Proc. Natl. Acad. Sci.* USA, 76:4350 (1979). The nitrocellulose membrane was treated with 3% BSA solution in PBS for 1 hour at room temperature to block any non-specific binding to antibodies in subsequent steps. The electroblotted proteins were probed with the Hn-33 antibodies by suspending the membrane overnight at 4° C. in 50 µg/ml antibody solution dissolved in 3% BSA. Unbound antibodies were removed by washing the membrane with 0.05% Tween-20™ in PBS four times using 200 ml of solution for each washing. Subsequently, the membrane was incubated for 1 hour at room temperature with anti-horse IgG-peroxidase conjugate at a 1:10,000 dilution in 3% BSA solution. The bound antibodies were detected by chromogenic oxidation of α-chloronaphthol. This procedure indicated that the affinity-purified Hn-33 antibodies recognized only a 33 kDa band.

Hn-33-specific antibodies completely blocked hemagglutination activity of Hn-33 and the complex at the higher antibody concentration. Hemagglutination activity elicited by 1.33 µg/ml of Hn-33 was blocked by 412 ng/ml of Hn-33 antibody, but not 206 ng/ml of antibody. However, the hemagglutination activity elicited by 1.33 µg/ml of type A neurotoxin complex was blocked by Hn-33 antibodies at both the 412 ng/ml and 206 ng/ml concentrations. The latter result indicated that Hn-33 is the only major hemagglutinin protein in the type A complex.

Example 3

Isolated, Biologically Active Hn-33 is Post-Translationally Modified

The N-terminal amino acid sequence of isolated, biologically active Hn-33 was determined as follows. About 10 pmoles of purified Hn-33 was dissolved in sample buffer (0.5 M sucrose, 15% SDS, 312.5 mM Tris, 10 mM EDTA) and subjected to electrophoresis on a 12.5% SDS-PAGE gel (0.75 mm thick, 8×9 cm mini-gel) using Mini-PROTEAN II electrophoresis cell (Bio-Rad). The proteins were then transferred to a PVDF membrane (Bio-Rad) in Towbin buffer (25 mM Tris, 192 mM glycine, and 20% methanol) using a Mini Trans-Blot electrophoretic transfer cell (Bio-Rad) at 60V overnight in an ice bath. Post-translational cleavage was examined using Edman degradation followed by analysis on an autosequencer (Applied Biosystem Model 473A, Biomolecular Protein Sequencing Facility of Baylor College of Medicine, Houston, Tex.).

The same protein that had appeared as a single homogeneous band on a SDS-PAGE gel using 0.2 M tricine, 10 mM Tris-HCl, 1 mM EDTA, and 2.5% SDS (pH 8.0), appeared as three distinct bands on the gels used to prepare the protein for sequencing. To confirm the origin of these bands, we sequenced the lower two bands, the upper band being identical to the previously isolated Hn-33. Proteins in both bands had the identical N-terminal sequence VIQNSLNDKI (SEQ ID NO:2). This sequence matched the sequence of Hn-33 at the +6 position (MEHYSVIQNSLNKDI; SEQ ID NO:3) as described in East et al., *Syst. Appl. Microbiol.*, 17:306-312 (1994). Therefore, the above result suggests that the mature protein exists as a post-translational cleavage product.

Example 4

The Secondary Structure of Hn-33 Includes β-Sheets

To analyze the secondary structure of isolated, biologically active Hn-33, the protein was subjected to a far-UV circular dichroism (CD) study and FT-IR spectroscopy. CD spectra were recorded on a Jasco J715 spectropolarimeter with a scanning speed of 20 nm per minute and a response time of 8 seconds, using a 1 mm pathlength quartz cuvette at room temperature. The protein concentration used for spectral recordings was 0.2 mg/ml. For the final comparison of control and SDS-treated spectra, a reference spectrum of SDS solution was subtracted. Secondary structure content was estimated by the method of Yang et al. (*Meth. Enzymol.*, 130:208-269, 1986).

Figure 5:
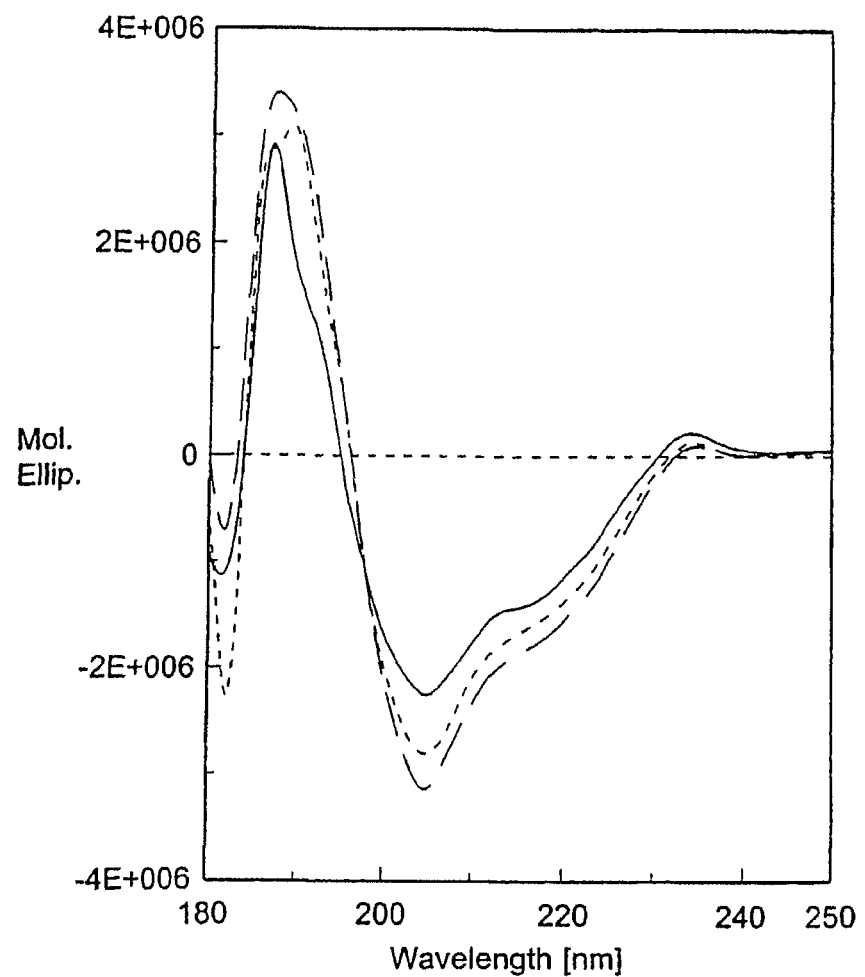
FIG. 5 is a graph of far-UV CD spectra of Hn-33.

Since treatment of Hn-33 with 0.05% SDS abolished biological activity (see Example 2), CD spectra of Hn-33 were collected in the presence and absence of submicellar (0.05%) and micellar (0.5%) concentration of SDS FIG. 5 is a series of spectra in which the solid line represents Hn-33 without SDS, the wide dashed line represents Hn-33 in the presence of 0.05% SDS, and the narrow dashed line represents Hn-33 in the presence of 0.5% SDS. The CD spectrum indicated a major negative peak at 205 nm and a positive band at 187 nm. Treatment of Hn-33 with 0.05% SDS significantly changed the shape of the CD spectrum, showing a shift of the negative peak at 205 nm. The positive CD band shifted from 187 to 190 nm. Treatment of Hn-33 with 0.5% SDS slightly increased the peak at 205 nm as compared to the 0.05% SDS spectrum. Secondary estimation suggested that Hn-33 was 6% α-helix, 55% β-sheets, and 39% random coils. In the presence of 0.05% SDS, the estimated composition shifted to 10% α-helix, 48% β-sheets, and 42% random coils. In the presence of 0.5% SDS, as compared to 0.05% SDS, the composition changed only in the percentage of random coils, and then only very slightly, to 10% α-helix, 48% β-sheets, and 41% random coils. Thus, treatment of Hn-33 with SDS increased the α-helix content and decreased the β-sheet content of the Hn-33 structure. However, little structural differences were seen in the Hn-33 polypeptide under submicellar and micellar concentrations of SDS.

The secondary structure of Hn-33 was additionally analyzed using a Nicolet 8210 FT-IR spectrometer as described in Fu et al., *Appl. Spectrosc.*, 48:1432-1441 (1994). One ml of a solution containing 0.65 mg/ml of Hn-33 was applied to a 60° horizontal zinc selenide, attenuated, total reflectance crystal. Spectra were built from 256 scans at a resolution of four per cm. All spectra were smoothed using a nine-point Savitsky-Golay algorithm and were multiplied by a factor of 100 for data analysis. An average spectrum was obtained from eight spectra which were recorded separately. For the secondary structure analysis, data processing was modified from the method of Fu et al. (1994), supra, by the use of LC software (LabCalc, Galactic Industries Co., Salem, N.H.). The Bassel deconvolution function was chosen with 3.3 as the gamma factor and 0.355 as the filter factor. The deconvolved spectra were first fitted with fixed band positions and floated half-height band width, and the band shaped to obtain the most reasonable band intensity for all individually resolved bands. Fixed band positions were released to obtain the best curve-fitting results. A computer calculation was used to float each parameter until the best fit (as determined by the best root mean square value) was obtained. The resulting parameter set was then applied to fit the bands into the original protein spectra to acquire the best resolved underlying bands. The amide I region was analyzed from 1550 to 1750 $cm^{-1}$, and the amide III region was analyzed from 1400 to 1200 $cm^{-1}$ to eliminate the contribution from the neighboring bands. The band assignments for various secondary structures were based on assignments used in Fu et al. (1994), supra.

Figure 6A:
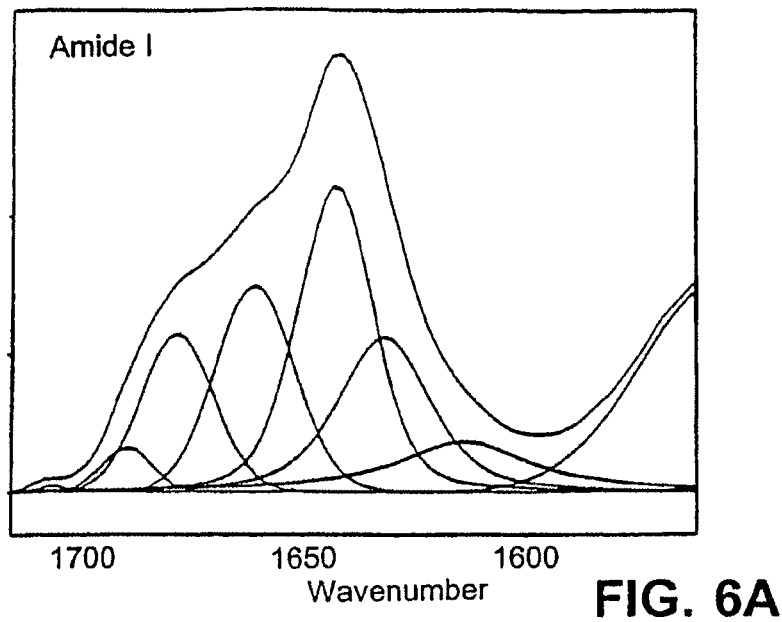
FIGS. 6A and 6B are graphs of IR spectra of Hn-33.
Figure 6B:
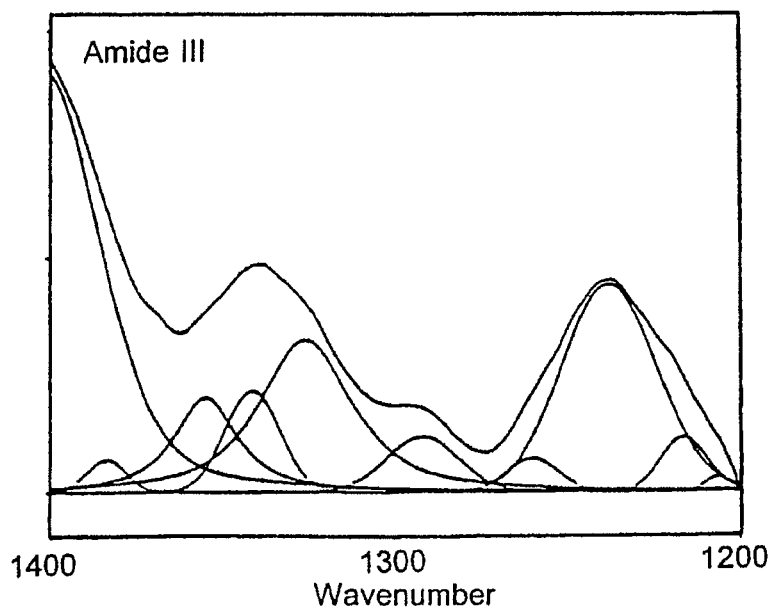

The amide I and III IR spectra of Hn-33 are shown in FIGS. 6A and 6B. Major absorption bands were observed at 1632 and 1237 $cm^{-1}$ in amide I and amide III regions, respectively, suggesting that β-sheets dominate the Hn-33 structure. Resolved band positions of amide I and III and their contributions and assignments to secondary structure types were determined. Based on the amide I band analysis, Hn-33 consists of 74% β-sheets, no α-helix, and 26% β-turns or unordered structures. Based on the amide III band analysis, Hn-33 consists of 77% β-sheets, no α-helix, and 23% β-turns or unordered structures. Despite small differences in the individual secondary structure types, data from the two amide regions were generally consistent and agreed with the far-UV CD analysis above.

The broad band observed at 1370 $cm^{-1}$ (FIG. 6B) is not commonly associated with proteins and may be indicative of a prosthetic group. We used a Schiffs reagent kit (Sigma, St. Louis, Mo.) per manufacturer's instructions and as described in Doerner et al., *Anal. Biochem.*, 187:147-150 (1990) to test for carbohydrates. No carbohydrates were found.

Example 5

Isolated, Biologically Active Hn-33 Is Protease Resistant

Biologically, active Hn-33 was isolated as described in Example 1 above. Digestion of Hn-33 was carried out as described in Deresiewicz et al., *Biochemistry*, 33:12844-12851 (1994). The degree of proteolytic fragmentation was monitored by performing SDS-PAGE on the digestion reaction followed by Western blotting as described above. Results are typically expressed as a percentage of intact polypeptide, referring to the amount of the polypeptide remaining as a full-length band on the SDS-PAGE gel. The percentage degraded is one hundred minus the percentage intact.

A relatively high concentration of trypsin (up to 1 mg/ml for 24 hours) did not degrade Hn-33. Under milder conditions (0.1 mg/ml for 30 minutes), the type A neurotoxin complex was degraded. The Hn-33 was resistant to proteolytic attack from all proteases tested, including α-chymotrypsin, subtilisin, and pepsin. Resistance was also observed under conditions of low pH (see conditions for pepsin below) or added carbohydrates.

The trypsin digestions was carried out by incubating Hn-33 with the protease at a 250:1 w/w ratio in 50 mM Tris (pH 7.0) and 5 mM $CaCl_2$. When carbohydrates (o-nitropheny-β-D-galactoside and isopropyl-β-D-thiogalactoside) were optionally added to a final concentration of 66.7 mM (a concentration that inhibited Hn-33 hemagglutination activity), the incubations were carried out at 25° C. for 30 minutes.

Digestions with other proteases were as follows: Pepsin digestions were carried out at a 25:1 protein: protease ratio in 50 mM ammonium acetate (pH 2.0) and 2 mM EDTA. α-Chymotrypsin digestions were carried out at a 1000:1 protein:protease ratio in 50 mM Tris (pH 7.8) and 5 mM $CaCl_2$. Subtilisin digestions were carried out at a 25:1 protein:protease ratio in 0.1 mM ammonium bicarbonate (pH 7.5) and 1 mM guanidine-HCl. Trypsin and α-chymotrypsin digestions were carried out at room temperature, and the pepsin and subtilisin digestions were carried out at 37° C. Digestions were stopped by the addition of 1 mM PMSF into the reactions. Stopped reactions were then boiled in SDS-PAGE running buffer before loading onto 8-25% gradient gels. Hn-33 was highly resistant (less than 5% of the polypeptide digested as shown on SDS-PAGE gels) to all proteases tested herein.

These results indicate that Hn-33 is resistant to a variety of proteases found in the GI tract and suggests that the polypeptide (or fragments or derivatives thereof) is stable if administered to the GI tract and would thus be useful to stabilize an oral vaccine composition.

Example 6

Isolated, Biologically Active Hn-33 Binds to Type A Neurotoxin and Protects the Resulting Complex from Proteolytic Degradation

Type A neurotoxin and Hn-33 were purified from *C. botulinum* type A as described in Example 1 above.

To determine direct binding between the neurotoxin and Hn-33, 5 mg of the neurotoxin was mixed with 1.7 mg Hn-33 in 3 ml 0.05 M sodium citrate, pH 5.5 (this corresponds to a 1:1.5 neurotoxin to Hn-33 molar ratio). The mixture was incubated for 30 minutes at room temperature before being applied to a Sephadex™ G-200 column (1.5×100 cm) which was previously equilibrated with 0.05 M citrate buffer, pH 5.5. The protein was eluted with the same buffer at a flow rate of 12 ml/h. The 1.7 ml fractions were collected, and the protein content was estimated by monitoring absorbance at 280 nm. Peak fractions were analyzed on 8-25% SDS-PAGE gels.

Two mg each of standard proteins (cytochrome C, 12.4 kDa; carbonic anhydrase, 29 kDa; BSA, 66 kDa; alcohol dehydrogenase, 150 kDa; and apoferritin, 443 kDa) were dissolved in 0.05 M sodium citrate, pH 5.5, and applied to Sephadex G-200 column and eluted in the manner described immediately above. Blue dextran was run along with the standard proteins to estimate the void volume of the column. Molecular weights of the peaks corresponding to Hn-33 and its complex with neurotoxin were estimated using a plot of the log of standard MW vs. standard Rf value.

Figure 7:
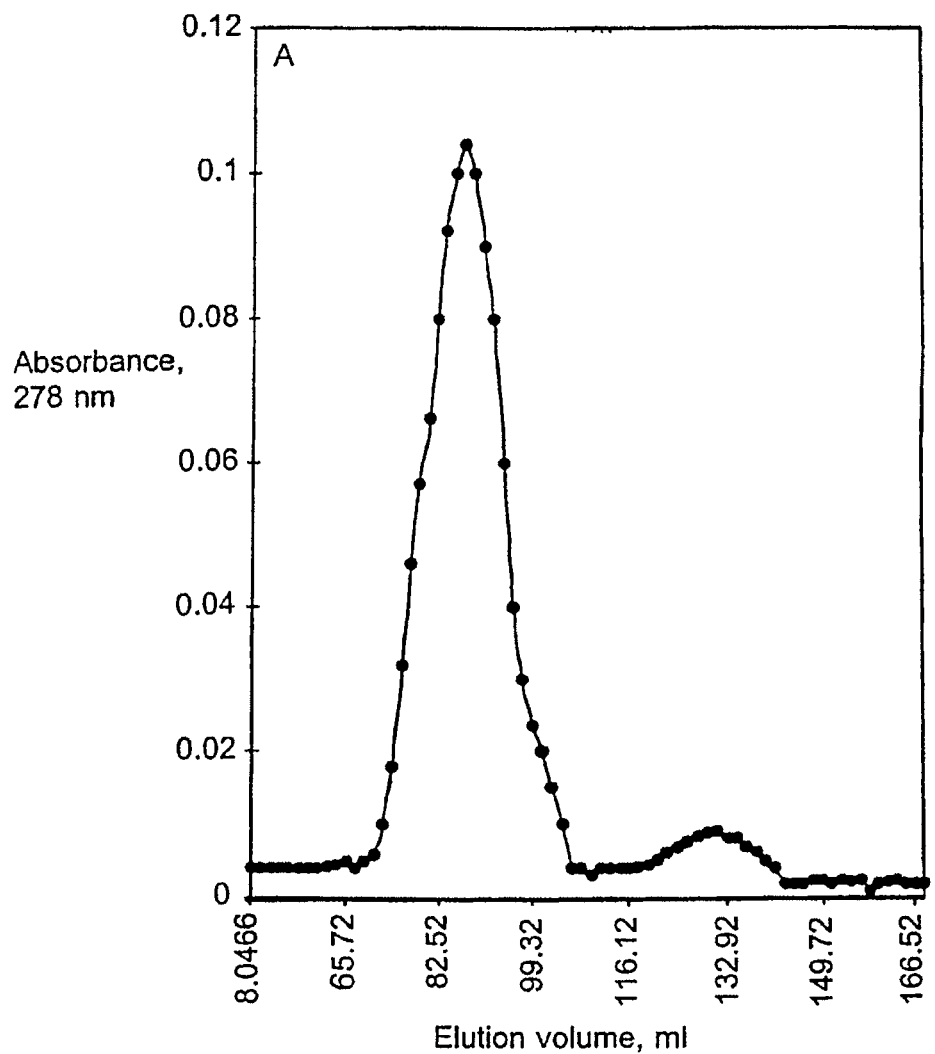

The Hn-33/neurotoxin mixture was eluted in two peaks (FIG. 7)0. Peak fractions were subjected to SDS-PAGE as described in Example 1, followed by COOMASSIE BLUE™ staining, indicating that the first peak contained a 140 kDa and a 33 kDa protein and the second peak contained only the 33 kDa protein. Based on the 280 nm absorbance and the SDS-PAGE, it was estimated that about 94% of the Hn-33 bound to the neurotoxin.

Neurotoxin alone, neurotoxin complex, or equal amounts of neurotoxin and Hn-33 (which were mixed together and incubated for 30 minutes at room temperature), were dialyzed for 30 minutes in digestion buffer specific for each protease and then subjected to digestions as described in Example 2. As expected, the neurotoxin complex remained at least 60% intact in digestions containing pepsin, trypsin, subtilisin, and α-chymotrypsin.

Pepsin began to digest the "naked" neurotoxin after 20 minutes and completely digested the neurotoxin after 60 minutes. When Hn-33 was included in the "naked" neurotoxin incubation, the neurotoxin remained at least 75% intact even after 90 minutes of digestion. Similar results were obtained when trypsin and chymotrypsin were used in separate experiments. These experiments indicate that Hn-33 can protect neurotoxins from proteolytic degradation under conditions which mimic the GI environment, including low pH and the presence epithelial cell surface carbohydrates. Thus, isolated, biologically active Hn-33 should protect a *botulinum* neurotoxin protein from proteolytic degradation.

Example 7

Use of Isolated, Biologically Active Hn-33 in Vaccines

One milligram of isolated, biologically active Hn-33 is incubated with one milligram of type A *botulinum* neurotoxin in phosphate-buffered saline to prepare an Hn-33 vaccine composition. After an incubation sufficient to allow binding of Hn-33 to the neurotoxin, the mixture is lyophilized and resuspended in 100 milliliters of sterile, deionized water to formulate the vaccine. The vaccine is administered by drinking.

For testing of the vaccine in an animal model, a rabbit is orally immunized via a feeding needle inserted into the rabbit's stomach with a vaccine containing 200 micrograms of the Hn-33/neurotoxin complex prepared as described above in this Example. The same quantity of saline without neurotoxin is administered to additional rabbits of the same type and weight as a control. Such vaccine administration is described in Karem et al., *Infect. Immun.*, 63:4557-4563 (1995). Rabbits are observed for signs of botulism symptoms. Two booster injections are made at a dosage of 200 micrograms Hn-33/neurotoxin complex each, the first booster at two weeks post-initial inoculation and the second booster at six weeks post-initial inoculation. Rabbits are again observed for signs of botulism.

After the initial and booster immunizations, sera and T-cells are tested for an immune response against the neurotoxin vaccine. All rabbits are then subcutaneously challenged with an $LD_{50}$ does of the corresponding neurotoxin or neurotoxin complex. Any changes in symptoms and death rates in immunized rabbits as compared to controls are noted and analyzed.

Example 8

**Isolated, Biologically Active Hn-33 Enhances *Botulinum* Neurotoxin Protease Activity**

To determine if Hn-33 could enhance the protease activity of the type A *botulinum* neurotoxin protein, the ability of the neurotoxin to cleave a SNAP-25-GST fusion protein in the presence and absence of Hn-33 was examined.

SNAP-25 is a membrane-associated protein implicated in the fusion of synaptic vesicles with the presynaptic membrane. *Botulinum* neurotoxin cleaves SNAP-25 at a site 9 and 26 amino acids from the C-terminus (Williams et al., *J. Biol. Chem.*, 271:7694-7699, 1996; and Sollner et al., *Nature*, 362: 318-324, 1993).

The SNAP-25-GST fusion protein was purified using standard methods which are described in Smith et al., *Meth. Molec. Cell. Biol.*, 4:220-229 (1993). The purified fusion protein was dissolved and dialyzed in 50 mM Tris, 10 mM sodium phosphate, 300 mM NaCl, 2 mM $MgCl_2$, 0.3 mM $CaCl_2$, 1 mM 2-mercaptoethanol, and 0.1% $NaN_3$ (pH 7.6, 4° C.).

Type A *botulinum* neurotoxin was purified as described in Example 1 above. Type E *botulinum* neurotoxin was purified as described in Gimenez et al., *Appl. Environ. Microbiol.*, 53:2827-2830 (1987) and modified as follows. The precipitated type E neurotoxin was dissolved in and dialyzed against 0.02 M sodium phosphate, pH 7.4, for 12 to 16 hours. The complex was then applied to a DEAE-SEPHADEX™ A-50 column equilibrated with the buffer immediately above. Unbound material was washed off with 10 column volumes of the buffer while most of the complex bound to the column. The type E neurotoxin was eluted with 0.2 M NaCl gradient until the A280 readings reached background levels.

Digestions were carried out in 0.01 M phosphate buffer (pH 7.4) containing 1.7 µM neurotoxin and 5 µM SNAP-25 fusion protein for 30 minutes at 37° C. 5 µg of Hn-33 was optionally added before the digestion. The digestions were optionally pre-incubated with 20 mM DTT for 30 minutes at 37° C. to reduce disulfide bonds. Digestions were then stopped by adding SDS-PAGE sample buffer and heating the digestion for 4 minutes at 100° C. A 30 μl sample was then resolved on a 12% SDS-PAGE gel and Western blotted using an antibody raised against the C-terminal 12 amino acids of SNAP-25. The amount of substrate cleaved was determined as described in Example 6 above.

Figure 8:
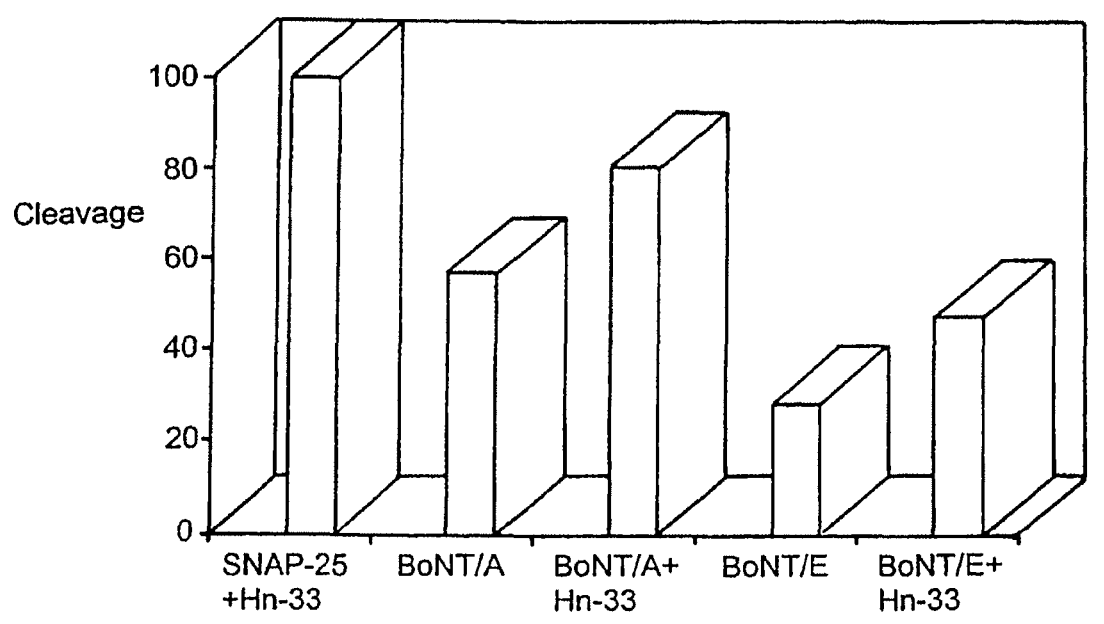

Type A neurotoxin cleaved 57% of the SNAP-25 fusion protein under the conditions described above while type E neurotoxin cleaved only 28% of the SNAP-25 fusion protein. In the presence of Hn-33, the type A neurotoxin cleaved 80% of the fusion protein and the type E neurotoxin cleaved 47% of the fusion protein (FIG. 8). Thus, addition of Hn-33 to the neurotoxins before digestion resulted in enhancement of substrate cleavage by *botulinum* neurotoxins, indicating that a therapeutic compositions containing Hn-33 and a neurotoxin can have a higher therapeutic activity. Such improved compositions are useful for patients requiring more neurotoxic activity or less administered drug due to side-effects caused by non-neurotoxin ingredients.

OTHER EMBODIMENTS

It is to be understood that while the invention has been described in conjunction with the detailed description thereof, the foregoing description is intended to illustrate and not limit the scope of the invention, which is defined by the scope of the claims. Other aspects, advantages, and modifications are within the scope of the following claims.

What is claimed is:

1. A composition comprising a purified, biologically active hemagglutinin-33 polypeptide (Hn-33) from type A *Clostridium botulinum*, a purified neurotoxin, and optionally a pharmaceutical carrier suitable for administration to an animal, wherein the Hn-33 is fused to a moiety selected from the group consisting of a histidine tag, a lacZ tag, a glutathione S-transferase (GST) tag, and an immunoglobulin Fc domain tag.

2. The composition of claim 1, wherein the pharmaceutical carrier is an adjuvant.

3. The composition of claim 1, wherein the pharmaceutical carrier is selected from the group consisting of polysorbates, ethanol, starch, and glycerin.

4. The composition of claim 1, wherein the neurotoxin is selected from the group consisting of type A *botulinum* neurotoxin, type E *botulinum* neurotoxin, and tetanus toxin.

5. The composition of claim 4, wherein the neurotoxin is type A *botulinum* neurotoxin.

6. The composition of claim 1, wherein the neurotoxin inhibits neurotransmitter release from a presynaptic membrane of a neurosensory junction and has protease activity.

7. The composition of claim 1, wherein the Hn-33 enhances the protease activity of the neurotoxin.

8. The composition of claim 1, wherein the biological activity of the Hn-33 comprises hemagglutination and the ability to protect the neurotoxin polypeptide from degradation in the gastrointestinal tract.

9. The composition of claim 1, wherein the moiety is a histidine tag.

10. A method of treating a neuromuscular condition involving a muscle spasm in an animal in need of said treatment comprising injecting into a muscle of said animal having the spasm or into a tissue surrounding the muscle, an amount of the composition of claim 1, wherein the amount is effective to treat the neuromuscular condition.

11. The method of claim 10, wherein the muscle having the spasm is a skeletal muscle.

12. The method of claim 10, wherein the muscle having the spasm is a smooth muscle.

13. The method of claim 10, wherein the composition further comprises a polymer that enables slow release of the composition.

14. The method of claim 10, wherein the neuromuscular condition is a headache.

15. The method of claim 10, wherein the animal is a human.

16. The method of claim 10, wherein the moiety is a histidine tag.

* * * * *